United States Patent
Lejeune et al.

(10) Patent No.: US 6,762,213 B2
(45) Date of Patent: Jul. 13, 2004

(54) BUFFER POLYMERS, CO-IMMOBILE BUFFER AND ENZYME POLYMERS AND METHODS OF SYNTHESIS THEREOF

(75) Inventors: Keith E. Lejeune, Pittsburgh, PA (US); Bryan Allinson, Pittsburgh, PA (US)

(73) Assignee: Agentase, LLC, Pittsburgh, PA (US)

( * ) Notice: Subject to any disclaimer, the term of this patent is extended or adjusted under 35 U.S.C. 154(b) by 0 days.

(21) Appl. No.: 10/215,337

(22) Filed: Aug. 8, 2002

(65) Prior Publication Data

US 2004/0030042 A1 Feb. 12, 2004

(51) Int. Cl.$^7$ .............................................. C08G 18/32
(52) U.S. Cl. ...................................... 521/164; 435/182
(58) Field of Search ........................... 521/164; 435/182

(56) References Cited

U.S. PATENT DOCUMENTS 4,734,475 A * 3/1988 Goldenberg et al.

OTHER PUBLICATIONS

LeJeune et al.; Biotechnol. Bioeng. 54, 105 (1997).*

* cited by examiner

*Primary Examiner*—Rachel Gorr
(74) *Attorney, Agent, or Firm*—Craig G. Cochenour; Buchanan Ingersoll PC

(57) ABSTRACT

A polyurethane polymer includes at least one buffer selected to adjust pH to a pH within a desired range. The buffer compound is immobilized within the polymer, and the polymer has a buffer capacity in excess of 3 micromoles of acid or base per gram polymer. A polymer includes at least one enzyme that is selected to catalyze a reaction of a substance. The enzyme is immobilized within the polymer. The polymer also includes at least one buffer selected to adjust the pH in the vicinity of the enzyme to a pH within a desired range. The buffer compound is also immobilized within the polymer. The polymer preferably has enzyme activity and a buffer capacity in excess of 3 micromoles acid or base per gram polymer. In one embodiment, each of the enzyme(s) and the buffer(s) are covalently bonded to the polymer.

32 Claims, 12 Drawing Sheets

Hepes  MES

BUFFER POLYMERS, CO-IMMOBILE BUFFER AND ENZYME POLYMERS AND METHODS OF SYNTHESIS THEREOF

The invention described herein was made in the course of work supported in part by the United States of America, Department of Defense, Contract No. DAMDI 7-99-C-9016. The Government may have certain rights in this invention.

BACKGROUND OF THE INVENTION

The present invention relates to immobile buffer polymers, co-immobile buffer and enzyme polymers (or polymers in which an enzyme and a buffer are immobilized) and to methods of synthesis of polymers including immobilized buffer and polymers including immobilized enzyme and immobilized buffer.

In general, the function of an enzyme is to catalyze chemical reactions. Enzymes have a wide range of applications. For example, industrial applications of enzymes include, but are not limited to, fermenting wine, leavening bread, curdling cheese, and brewing beer. Medical applications of enzymes include, but are not limited to, killing disease-causing microorganisms, promoting wound healing, and diagnosing certain diseases.

In general, six classes of enzymes are recognized, which include oxidoreductases, transferases, hydrolases, lyases, isomerases, ligases. Oxidoreductases catalyze oxidation or reduction reactions and are referred to as Enzyme Class 1 enzymes (EC1). Transferases catalyze the transfer of specific radicals or groups and are referred to EC 2 enzymes. Hydrolases catalyze hydrolysis reactions and are referred to as EC 3 enzymes. Lyases catalyze removal from or addition to substrate specific chemical groups and are referred to as EC 4 enzymes. Isomerases catalyze isomeration reactions and are referred to as EC 5 enzymes. Ligases catalyze reactions which combine or bind together substrate units and are referred to as EC 6 enzymes. These classifications cover generally all enzymes used in industrial, medical, and other applications.

The biocatalytic activity of enzymes in industrial, medical or other applications occurs within a range of environmental conditions (for example, pH, temperature, pressure, and ionic strength) similar to the typical biological environment of the enzymes. Each enzyme within the six enzyme classifications has, for example, an optimal pH range, in which the rate of enzyme catalyzed reaction is the fastest. This optimal pH range (as well as optimal ranges for other environmental conditions) can be narrow or broad, depending on the enzyme. Typically, plant-based enzymes have broader pH ranges than animal-based enzymes.

One method of maintaining optimal pH is to neutralize acid or base in solution. Buffer salts, for example, can be added to "initialize" the pH or add buffer capacity to solution. In fact, addition of buffer is the most common method for maintaining high catalytic rates for laboratory and industrial enzymatic reactions. Hydrolase enzymes (EC 3) are of special interest because they produce acid or base as a byproduct and, thus, can alter the pH of an unbuffered solution during the course of a reaction. Examples of such hydrolases includes pectinase, protease, urease, and organophosphorous hydrolase (OPH). Pectinases break down cell walls to clarify fruit juices. Proteases in detergents break down protein-based stains. Urease breaks down urea in urine into carbon dixoide and ammonia. OPH degrades organophosphates into byproducts. Pectinases, proteases, and OPH create an acid ($H_3O^+$) as byproduct. Urease creates a lewis base ($NH_4^+$) as byproduct.

Over time, the tertiary or three-dimensional structure of an enzyme may erode and the enzyme (and its active site) may correspondingly lose integrity, especially at high temperatures. This process is called enzyme denaturation. The enzyme and its active site are in proper conformation when ideal physiological conditions of, for example, moderate temperature, pH, and ionic strength are present. Seemingly minor changes in these conditions may cause changes in protein folding, resulting in catalytic activity loss and permanent denaturation. To protect against denaturation, enzymes can be immobilized on or within a solid polymer to rigidify and stabilize enzyme chemical structure. Through chemical modification, immobilization masks sensitive residues in the enzyme's protein structure. Immobilized enzymes maintain their activity over a broader set of environmental conditions than native enzymes, including residence time in solution and temperature. By attaching an enzyme within a polymeric matrix as described, for example, in LeJeune, K. E., Mesiano, A. J., Bower, S. B., Grimsley, J. K., Wild, J. R., Russell, A. J., Biotechnol. Bioeng. 54, 105 (1997) (sometimes referred to herein as "LeJeune et al. (1997)"), enzyme stability is greatly enhanced.

Immobilization does not, however, protect enzymes against activity loss associated with extreme pH environments (that is, environments in which the pH is outside of the optimal pH range or well outside the optimal pH range). Both native and immobilized enzymes lose activity when placed in extreme pH environments or when significant quantities of acidic or basic byproducts are produced. For example, immobilized urease will continue to degrade urea into ammonium ion byproduct in distilled water, but when sufficient quantities of byproduct are generated, the pH rises. Immobilized urease loses activity as pH levels rise above the optimal pH and loses all activity at around pH 10. A similar effect is observed with OPH, which will degrade methyl parathion and generate acid byproduct in an unbuffered environment until reaching pH 4.

In general, immobilized enzymes are of limited use in catalyzing reactions in environments in which pH is outside of the optimal pH range of the enzyme. Moreover, immobilized hydrolases (EC 3) are of limited use in catalyzing reactions in unbuffered environments. Thus, immobilized enzymes require an added buffer to neutralize acid or base when placed in a solution with a pH outside the active range or the optimal pH range of the immobilized enzyme. Immobilized hydrolases require an added buffer to neutralize acid or base byproducts, which alter the pH to a pH outside of the active range or the optimal range of the immobilized hydrolase enzyme. However, it may not be practical or possible to add buffer to an environment in which an immobilized enzyme is to be used. For example, in field use for decontamination of a toxic agent or agents in which a large area must be decontaminated, addition of buffer may not be practical and/or buffer may not be available. Currently available immobilized enzymes cannot, therefore, be used to their full advantage in certain environments.

It is desirable, therefore, to develop immobilized enzyme systems and methods that reduce or, preferably, eliminate the above and other problems.

SUMMARY OF THE INVENTION

In one aspect, the present invention provides a polyurethane polymer including at least one buffer selected to adjust pH to a pH within a desired range. The buffer compound is immobilized within the polymer, and the polymer has a buffer capacity in excess of 3 micromoles of acid or base per gram polymer. Preferably, the polymer has a buffer capacity in excess of 60 micromoles acid or base per gram polymer. More preferably, the polyurethane polymer has a buffer capacity in excess of 100 micromoles acid or base per gram polymer. Even more preferably, the polyurethane polymer has a buffer capacity in excess of 200 micromoles acid or base per gram polymer. As described further below, attempts to incorporate significant buffer capacity in polyurethane polymers have been unsuccessful. The immobile buffer polyurethanes of the present invention provide polymers having significant buffer capacity over a wide range of polymer physical characteristics (for example, density and pore size).

In another aspect, the present invention provides a method for preparing a polyurethane polymer immobilizing at least one buffer comprising the steps: reacting a buffer compound with a multifunctional precursor for the polyurethane polymer to produce a modified precursor, the buffer compound having at least one functional group for reacting with the precursor and at least one buffering group that remains functional as a buffer after the buffer compound is reacted with the precursor; and subsequent to reacting the buffer compound with the precursor, polymerizing the modified precursor to form the polyurethane polymer.

The polyurethane polymer can, for example, be formed by first reacting the buffer compound with an isocyanate functionalized polyurethane precursor to produce a modified polyurethane precursor. Water and the modified polyurethane precursor can be mixed to form a polyurethane foam. In general, buffer immobilizing polyurethanes of a wide range of polymer physical properties can be synthesized in the present invention using modified polyurethane precursors as described above and known polymerization techniques.

In a further aspect, the present invention provides a polymer including at least one enzyme that is selected to catalyze a reaction of a substance. The enzyme is immobilized within the polymer. The polymer also includes at least one buffer selected to adjust the pH in the vicinity of the enzyme to a pH within a desired range. The buffer compound is also immobilized within the polymer. The polymer preferably has greater than 2% enzyme activity retention. In that regard, the polymers of the present invention generally incorporate approximately 0.01 to 5 wt % enzyme. Of the total enzyme loaded, preferably at least 2% of enzyme activity is retained as compared to the activity of the native enzyme. The polymer also preferably has a buffer capacity in excess of 3 micromoles acid or base per gram polymer. In one embodiment, each of the enzyme(s) and the buffer(s) are covalently bonded to the polymer. The enzyme and buffer content of such co-immobile buffer and enzyme polymer of the present invention can be tailored for use in specific environments. In one embodiment, the polymer can, for example, preferably have greater than 8% enzyme activity retention, and a buffer capacity in excess of 60 micromoles acid or base per gram polymer. In another embodiment, the polymer preferably can have greater than 15% enzyme activity retention and a buffer capacity in excess of 3 micromoles acid or base per gram polymer. In still another embodiment, the polymer can preferably have greater than 2% enzyme activity retention and a buffer capacity in excess of 200 micromoles acid or base per gram polymer.

In several embodiments, the polymer is a polyurethane. The polyurethane can, for example, be a foam having an average pore size of at least approximately 0.1 mm. More preferably, the polyurethane foam has an average pore size of at least approximately 0.2 mm. In general, average pore size is preferably sufficiently large to enable diffusion of substrate into pores to interact with immobilized enzyme and sufficiently large to enable diffusion of reaction products out of pores. The polyurethane foam preferably has a density no greater than approximately 0.4 g/cm$^3$. More preferably, the polyurethane foam has a density no greater than approximately 0.2 g/cm$^3$.

In another aspect, the present invention provides a system for catalyzing a reaction of at least one substance in an environment The system includes at least one enzyme that is selected to catalyze a reaction of the substance and at least one buffer compound selected to adjust the pH in the vicinity of the enzyme to a pH within a desired range. Each of the enzyme and the buffer compound are covalently bonded within a single polymer. The polymer preferably has greater than 2% enzyme activity retention, and a buffer capacity in excess of 3 micromoles acid or base per gram polymer. In one embodiment, the single polymer is a polyurethane as described above.

In a further aspect, the present invention provides a method for preparing a polymer immobilizing at least one enzyme and at least one buffer including the steps: reacting a buffer compound with a multifunctional precursor for the polymer to produce a modified precursor, the buffer compound having at least one functional group for reacting with the precursor and at least one buffering group that remains functional as a buffer after the buffer compound is reacted with the precursor; and subsequent to reacting the buffer compound with the precursor, polymerizing the modified precursor in the presence of the enzyme to bond the enzyme to the polymer.

Once again, the polymer can be a polyurethane. In one such embodiment, the polymer is formed by first reacting the buffer compound with an isocyanate functionalized polyurethane precursor to produce a modified polyurethane precursor. The enzyme, water and the modified polyurethane precursor can, for example, be mixed to form a foamed polyurethane polymer.

In still another aspect, the present invention provides a method for preparing a modified polymer precursor for synthesis of a buffer immobilizing polymer including the step of reacting a multifunctional buffer compound with a multifunctional precursor for the polymer to covalently bond the buffer compound to the precursor compound via reaction of one of the functional groups of the buffer compound with one of the function groups of the polymer precursor, thereby producing the modified polymer precursor. The attached buffer compound has at least one functional group remaining after attachment to or incorporation within the modified polymer precursor that retains buffer capacity. The modified polymer precursor retains at least one functional group thereon suitable to react in a subsequent polymerization to synthesize the buffer immobilizing polymer. The multifunctional polymer precursor can, for example, include at least one isocyanate group. The multifunctional polymer precursor can also, for example, include at least two isocyanate groups.

As used herein, the phrase "immobile buffer polymer refers to a polymer in which on or more buffers are immobilized. As used herein, the phrase "co-immobile buffer and enzyme" and/or the phrase "co-immobile buffer and enzyme polymer" refer to a polymer in which both one or more buffers and one or more enzymes are immobilized. The co-immobile buffer and enzyme polymers of the present invention are capable of buffering acid or base from solution, thereby returning the solution to a pH within a desired range. Moreover, the, co-immobile buffer and enzyme polymers of the present invention are preferably reusable, not losing significant buffer capacity or significant enzyme activity following repeated consecutive uses. In the presence of one or more immobilized enzymes, a co-immobilized buffer or buffers also serve to neutralize acidic or basic products (for example, from hydrolysis reactions) that would otherwise negatively impact enzyme performance.

By effectively incorporating immobilized buffer and enzyme together in the polymers of the present invention, the resultant buffered enzymes have high buffer capacity and high activity in the environments having a range of initial pH.

To be immobilized within a polymer, buffers preferably have at least one reactive functional group suitable to form a connecting interaction within the product macromer or polymer and at least one remaining (that is, remaining after such a connecting interaction is formed) buffering functional group suitable to neutralize acid or base in solution. Preferably, the buffer includes a functional group that is suitable to form a covalent bond within the polymer. However, the buffer can also be immobilized within the polymer via non-covalent linkages such as via strong van der waals interactions or via an ionic interaction or bond. As known in the art, to be immobilized as described herein, enzymes preferably retain significant activity following immobilization.

Regardless of the manner of immobilization, the present inventors have discovered that the overall immobilized buffer capacity of a polymer incorporating immobilized buffer can be substantially increased as compared to prior attempts to immobilize buffer or co-immobilize buffer and enzyme within a polymer matrix by first interacting or reacting the buffer with an immobilizer/stabilizer suitable to form an interactive connection (for example, a covalent bond) with buffer prior to polymer or macromer formation. Preferably, the immobilizer/stabilizer is a precursor for the product polymer. The resultant modified polymer precursor is subsequently reacted in a known manner (or polymerized) to form the desired polymer product.

It is believed that the reactivity of the buffer alters the chemical reactions occurring during polymer or macromer formation when one attempts to incorporate buffer into a polymer during polymer formation as done in current synthetic procedures. In other words, the high degree of reactivity between buffer and polymer precursor(s) (that is, a monomer, a dimer, an oligomer (generally, a molecule having less than ten repeat units), or a prepolymer (generally, a molecule having a number average molecular weight of less than 50,000)) is believed to alter the polymerization process in current synthetic procedures. As a result, the polymers synthesized in such current synthetic procedures have poor physical characteristics, low buffer capacity and poor enzyme activity in environments of uncontrolled or unbuffered pH.

To the contrary, the immobile buffer polymers and the co-immobile buffer and enzyme polymers of the present invention, exhibit both desirable physical characteristics and retain high buffer capacity. In general, the incorporation of buffer or the incorporation of buffer and enzyme into the polymers of the present invention does not substantially alter the underlying polymerization as compared to standard polymerizations (that is, polymerizations without immobilize buffer or enzyme). The stabilization of the buffer via, for example, forming an interactive connection or bond with the polymer precursor reduces the reactivity of the buffer during the polymerization step and allows the reaction to proceed in a manner in which desirable polymer properties can be achieved in a controlled manner.

Moreover, co-immobile buffer and enzyme polymers of the present invention can be prepared in a wide variety of physical forms and morphologies such as fabrics, foams, gels, rubbers, and plastics using polymerization techniques known in the art. For example, co-immobile buffer and enzyme polymer of the present invention are readily prepared as foams such a polyurethane foams. Other foams can be prepared from, for example, polyethylene (PEG)-modified enzyme and buffer. In such a polymer, enzyme and buffer can, for example, be bonded together to a functionalized PEG such as PEG diisocyanate. Representative co-immobile buffer and enzyme polymeric gels of the present invention include, but are not limited to, urethane, acrylate, and other types of gels wherein buffer and enzyme can, for example, be immobilized through covalent linkage.

The co-immobilized polymers of the present invention can be used in many different applications, including, but not limited to, reusable pesticide decontaminating and detoxifying pads for cleaning spills or equipment and polymer cartridges for detoxifying large volumes of contaminated pesticide water. In another application, buffer and hydrolase enzyme co-immobilized polymers of the present invention can be used to decontaminate and detoxify chemical nerve agents such as soman without loss of activity associated with pH. In that regard, degradation of soman results in high amounts of acid byproduct.

The present invention, along with the attributes and attendant advantages thereof, will best be appreciated and understood in view of the following detailed description taken in conjunction with the accompanying drawings.

DETAILED DESCRIPTION OF THE INVENTION

Figure 1:
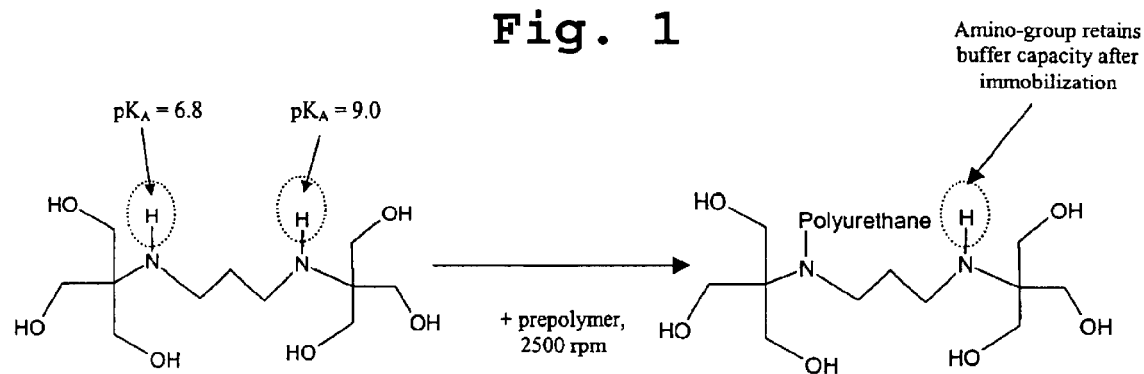
FIG. 1 illustrates the immobilization of bis-tris propane buffer within a polyurethane polymer.

The co-immobile buffer and enzyme polymers of the present invention exhibit high activity in unbuffered or extreme pH environments by maintaining pH in a desired range for high enzyme activity. When a co-immobile buffer and enzyme polymer is placed in substrate solution at a pH outside of the optimal range of the enzyme, the immobile buffer rapidly neutralizes acid or base to return the pH to within the optimal range. Once extreme pH has been neutralized, the immobile enzyme quickly begins to catalyze the reaction. The enzyme activity, buffer capacity and general utility of immobilized enzyme (wherein pH affects enzyme activity) is thus significantly enhanced in the present invention.

In a representative embodiment of the present invention, the enzyme activity of an enzyme of a co-immobile buffer and enzyme polymer is within its optimal range at moderate or relatively neutral pH levels. The co-immobile buffer quickly returns the pH to moderate levels when the polymer is placed in environments in which the pH is well outside of the optimal range for the enzyme. The amount of buffer and enzyme polymer required in a particular environment or use is a function of the amount of acidic ions ($H_3O^+$ or lewis acids) or of basic ions ($OH^-$, Lewis bases) the buffer must neutralize, which is a function of both initial pH and volume. In a representative example, 2 grams of 13% immobile buffer polymer returned the pH of 100 milliliters of an unbuffered solution from 3 to 7, while 200 milligrams of the same polymer returned the pH of 5 milliliters of solution from 3 to 7.

The efficacy of the co-immobilized buffers and enzymes of the present invention is not, however, limited to enzymes for which a moderate or neutral pH is optimal. Immobile buffer polymers can be tailored for use with enzymes having an optimal pH at any level. For example, the optimal pH for reduction of carboxyl groups by alcohol dehydroxenase (EC 1) is pH 6.7, whereas the optimal pH for oxidation of carboxyl by this enzyme is 9. Co-immobile buffer and enzyme polymers can be readily tailored to provide buffer capacity at either one of these pH levels or at virtually any other pH level as desirable for a particularly enzymatically catalyzed reaction.

The co-immobilized buffer and enzyme polymers of the present invention are especially useful when the enzyme is a hydrolase (EC 3), because co-immobile buffer neutralizes byproduct acid or base produced during hydrolase enzyme catalysis in solution. In that regard, conversion of substrate into product(s) alters the pH of an unbuffered solution given sufficient substrate levels. The higher the substrate levels, the greater the pH change associated with these changes. For example, immobilized DFPase (EC 3) used to hydrolyze soman produces acidic byproducts as the pH quickly drops around 4. In the case of immobilized DFPase without buffer, activity levels decrease with decreasing pH, and the enzyme no longer hydrolyzes soman at a pH of 4. In contrast, co-immobilized DFPase and buffer continues to hydrolyze soman without activity loss.

As with acid-producing enzymes, immobilized buffer initializes the pH of a solution in the case of base-producing hydrolase enzyme. As the immobilized enzyme catalyzes the hydrolysis of substrate into a basic byproduct, the immobilized buffer quickly neutralizes it. The reaction proceeds to completion (that is, until all of the substrate is hydrolyzed). To the contrary, in reactions with either native enzyme or immobilized enzyme (without buffer), pH levels quickly rise as byproducts are produced. The enzyme loses activity and may be denatured in the high pH environment.

Certain aspects of the present invention are discussed herein in the context of representative immobile buffer polymers and co-immobile buffer and enzyme polymers wherein buffer and enzyme are covalently bonded to the polymer. Specific examples include co-immobile bis-tris propane and OPH polyurethanes and co-immobile bis-tris propane and DFPase polyurethanes.

As described above, buffers for use in the present invention preferably have at least one reactive functional group suitable to form a connecting interaction or bond within the product macromer or polymer and at least one remaining buffering functional group suitable to neutralize acid or base in solution. The interactive functional group of the buffer can, for example, react with a polymer precursor (that is, a monomer, dimer, oligimer or prepolymer) to form a covalent bond therewith prior to polymerization. Buffers not having interactive or reactive functional groups, such as phosphate, sulfate, MES, and hepes, referred to herein as "unreactive" buffers, cannot be immobilized via covalent bonding within a polymer matrix. Buffers molecules such as tris (2-Amino-2-hydroxymethyl-1,3-propanediol) which have only one interactive or reactive functional group, which is also the loan buffer group, can be immobilized into a polymer via covalent bonding; however, the molecule loses all buffer capacity when so incorporated.

Free enzyme is preferably bound to polymers of the present invention by covalent linkages with a polymer precursor such as a monomer, a dimer, an oligomer, or a prepolymer during a polymerization step. Connective or bridging linkages formed between reactive functional groups on the enzyme and reactive functional groups on the precursor include, but are not limited to, amide, urea, urethane, and secondary amine. In general, the enzyme reactive functional groups are electrophillic while the precursor functional groups are nucleophillic. Another type of connective group or bridge is a disulfide bridge formed by covalent linkage between thio groups on the enzyme and on a precursor. Available reactive functional groups on enzymes include, for example, amine groups on lysine amino acid residues; thio groups on cysteine residues; and amide groups on arginine, asparigine, and glutamine residues. In some cases, unbonded amine groups on an amino acid bound to a protein chain may react with a functional group on a monomer or prepolymer to form a stable covalent bond. Reactive functional groups on polymer precursors include a broad range of functional groups able to react with amines, thios, or amides on the enzyme.

Isocyanate groups on, for example, toluene diisocyanate prepolymer represent one example of a functional group suitable to form a covalent linkage with an buffer or an enzyme in polyurethane chemistry. Solubilized enzyme and buffer immobilization can also be effected through polyethylene glycol chemistry. Further examples of functional groups for immobilization of enzyme and/or buffer include, but are not limited to, isocyanate groups on PEG-diisocyanate, maleimide groups on NHS-maleimide, and vinyl groups on PEG-acrylate.

For buffers with at least one reactive functional group (for example, a primary or a secondary amine group), increasing buffer content even by a relatively small amount (for example, by approximately 5%) under current synthetic techniques (in which, buffer or enzyme and buffer are simultaneously immobilized within the polymer matrix during polymerization) results in non-uniform polymers with poor physical properties. Such "reactive" buffers include, for example, bis{tris[hydroxymethyl]methylamino}propane (bis-tris propane), glycine dipeptide (gly-gly, or glycylglycine), N-(2-acetamido)-2-aminoethanesulfonic acid (aces), selenosemicarbazide (ssc), and tricine among others.

In a number of studies of the present invention, bis-tris propane (bis-tris) buffer, which contains two secondary amine groups, was immobilized within buffer immobile polymers and within a co-immobile buffer and enzyme polymers. The two amine groups of bis-tris buffer give the buffer two $pK_A$ values in solution. When reacted with monomer, prepolymer, or functionalized PEG, or other polymer precursor able to form a covalent bond with the buffer; one of the amine functional groups on the buffer forms a covalent linkage with the immobilizing agent, while the other functional group remains available as a buffer. Other examples of reactive, di-functional buffers suitable for use in the present invention include, but are not limited to, gly-gly and tricine. Gly-gly is a dipeptide having two amine functional groups, one of which can be used for covalent linking and the other for buffering. Tricine has an amine group and a carboxylic acid group and has two $pK_A$ values. In that regard, $pK_{A1}$, is pH 2.3, and $pK_{A2}$ is 8.1-8.6, wherein the carboxylic acid group is responsible for $PK_{A1}$, and the amine group responsible for $pK_{A2}$. Following immobilization of the buffer via amine functionality, immobilized tricine maintains its buffering capabilities at $pK_{A1}$, (pH 2.3). In general, any polypeptide or protein makes a good buffering agent as a result of its amine functionality.

In general, the present inventors have discovered that overall immobilized buffer capacity can be increased substantially as compared to prior attempts to incorporate buffer into a polymer matrix by first reacting the buffer with an immobilizer/stabilizer (a polymer precursor) able to form a covalent bond with buffer prior to a polymerization step. For example, when used to synthesize polyurethane foams, an increased level of reactive buffer content under current synthetic procedures results in foams with low buffer capacity. Attempting to increase buffer capacity by utilizing more buffer under current synthetic procedures results in polymers with poor physical properties. For example, resultant polyurethane polymers produced using current synthetic methods are not uniform, but are thick, sticky, plasmic mixtures that form a dense solid following evaporation of residual water content. Once again, the high degree of reactivity between buffer and prepolymer (or monomer) is believed to alter the polymerization process.

The two-step synthetic procedure of the present invention, which includes a buffer immobilization, stabilization or functionalization step decreases the reactivity of buffer toward prepolymer (or monomer) without decreasing buffer capacity. Polymers formed using the synthetic method of the present invention have high overall buffer capacity and good physical properties.

In several studies of the present invention, buffer and enzyme were immobilized into a polyurethane foam matrix using a synthetic technique based upon that described in LeJeune el. al (1997), and in LeJeune, K. E. and Russell, A. J. Biotechnol. Bioeng. 51, 450 (1996) for comparison to polymers synthesized using the synthetic methods of the present invention. The studies of the present invention indicate that one can increase the amount of buffer that can be immobilized within polyurethane polymers (for example, foams) by reacting electrophilic functional groups on buffer molecules with a polymer precursor (for example, toluene diisocyanate (nucleophilic)) prior to polymerization and enzyme immobilization. The synthetic technique of the present invention produced polyurethane foams with high porosity and low density, while maintaining high buffer capacity and enzyme activity. It is believed that the above-described "buffer pretreatment" creates buffer-prepolymer oligomers having many buffer functional groups and few reactive functional groups. Without such pretreatment, it is believed that reactive functional groups on the buffer (for example, bis-tris propane) and toluene isocyante react with each other quickly and vigorously during synthesis to form polymers with poor physical properties, low enzyme activity, and low buffer capacity. Only 4% by weight maximum of bis-tris propane buffer may be immobilized in polyurethane foams when using the current one-step method described, for example, in LeJeune el. al (1997), and LeJeune, K. E. and Russell, A. J. Biotechnol. Bioeng. 51, 450 (1996) (in which no buffer functionalization occurs prior to the polymerization reaction). However, more than 13% by weight bis-tris propane buffer was immobilized in foams when using a with the two-step method (reacting/treating buffer with diisocyanate prepolymer prior to reaction) of the present invention.

EXPERIMENTAL EXAMPLES

Example 1

Incorporation of Buffer within Polymer

In several initial studies of incorporation of buffer into polymers, we synthesized a number of different polymers using methods generally described in LeJeune et. al. (1997). Using those methods, equal volumes of aqueous solution and Hypol 3000 polyurethane prepolymer were stirred for 30 seconds at 2500 rpm with a custom-designed mixer head. Aqueous solutions were prepared containing various concentrations (0 to 500 mM) of buffer. Tris, phosphate, hepes, MES, and bis-tris propane buffer were studied.

The buffer content of resultant polymers ranged from around 0 to 6% by weight following curing. Polymers synthesized with phosphate, hepes, and MES buffer-containing aqueous solution had good physical properties and did not gel into a dense material. However, as described further below, phosphate, hepes, and MES buffers do not contain functional groups reactive with the polyurethane prepolymer and were not permanently immobilized in the polymer. On the other hand, polymers synthesized with aqueous solution containing bis-tris propane and tris buffer, which do include reactive functional groups and were permanently immobilized in the polymer, gelled into a dense, sticky material above approximately 4% buffer content. At 1 to 2% buffer content (100 to 200 mM in synthesizing solution), polymers synthesized with aqueous solution containing bis-tris propane and tris buffer appeared dense and rigid.

Polymers (100 mg) of each buffer type were placed in 100 ml tap water. We recorded the initial pH and spiked the solution with 200 μl of 3.8% hydrochloric acid (2 mM HCl in solution). We then monitored the pH change over time. Because tris buffer includes only one functional group (an amino group), which is also the buffer group, polymers incorporating tris buffer did not retain buffer capacity and there was no pH change over time. Each of bis-tris propane, MES, and hepes polymers retained buffer capacity and reduced pH in the first use as set forth in Tables 1-3 below. After the first use as described above, the polymers were rinsed in a dishwasher for one hour with 55° C. water to rinse out residual acid. We then conducted another acid spike experiment as described above. Essentially, we spiked the unbuffered solution containing buffer polymer with hydrochloric acid and monitored the pH change over time. We repeated this process several times to determine whether or not buffer capacity is retained with repeated use. Of the buffer polymers tested, only bis-tris propane maintained its buffer capacity over multiple titrations as set forth in Tables 1-3.

TABLE 1

Bis-tris propane polymers increase pH when used consecutively.

| Time after adding 200 ml of 3.8% HCl | First use | Wash at 55° C., use again | Wash, use a third time | Wash, use a fourth time |
|---|---|---|---|---|
| Prior to adding acid (Initial pH) | 8.63 | 7.41 | 7.22 | 8.05 |
| 1 min | 3.95 | 4.06 | 3.69 | 3.75 |
| 20 min | 4.7 | 4.19 | 3.81 | 4.14 |
| 1 hour | 5.5 | 4.44 | N/A | 4.49 |
| 2 hour | 5.74 | 4.55 | N/A | 4.63 |

TABLE 2

MES polymers increase pH for the first use, but do not increase pH when used consecutively.

| Time after adding 200 ml of 3.8% HCl | First use | Wash at 55° C., use again | Wash at 55° C., use a third time |
|---|---|---|---|
| Prior to adding acid (Initial pH) | 8.25 | 8.18 | 8.59 |
| 1 min | 5.48 | 3.9 | 3.81 |
| 20 min | 6.1 | 3.94 | 3.88 |
| 1 hour | 6.26 | 3.94 | 3.91 |
| 2 hour | N/A | 3.9 | 3.85 |

TABLE 3

Hepes polymers increase pH for the first use, but do not increase pH when used consecutively.

| Time after adding 200 ml of 3.8% HCl | First use | Wash at 55° C., use again | Wash at 55° C., use a third time |
|---|---|---|---|
| Prior to adding acid (Initial pH) | 8.16 | 8.5 | 8.11 |
| 1 min | 3.56 | 3.8 | 3.71 |
| 20 min | 3.95 | 3.86 | 3.8 |
| 1 hour | 6.05 | 3.89 | 3.84 |
| 2 hour | 6.53 | 3.9 | 3.85 |

Results from bis-tris propane polymers in Table 1 demonstrated that bis-tris propane polymers provide reusable buffer capacity. The reusability is a result of bis-tris buffer having two available amino groups: one to act as a buffer, and the other to react with prepolymer for immobilization. FIG. 1 illustrates the chemical structure of bis-tris buffer before and after immobilization. Subsequent studies set forth below indicated that higher levels of bis-tris propane immobilization provide higher buffer capacity.

Figure 2B:
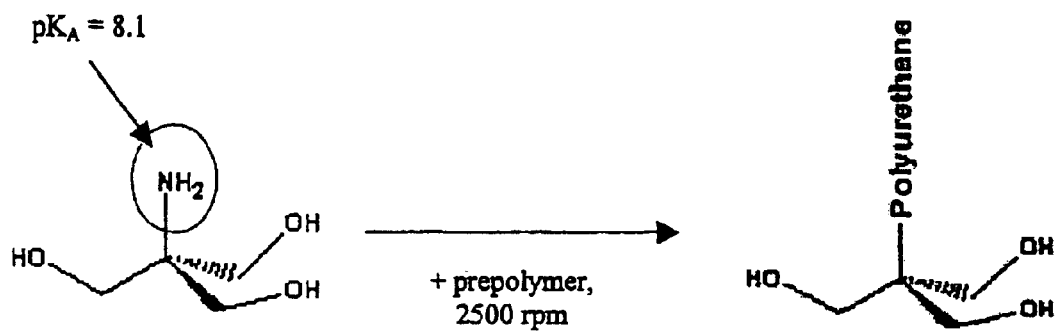
FIG. 2B illustrates the immobilization of bis buffer within a polyurethane polymer and the associated loss of buffer capacity of bis buffer.
Figure 2A:
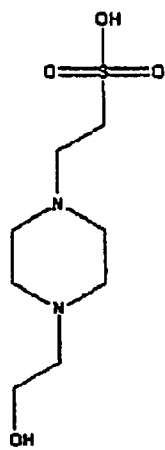
FIG. 2A illustrates the structures of Hepes buffer and MES buffer.
Figure 2A:
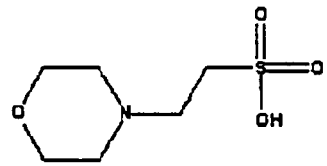

Both "unreactive" buffers tested, MES and Hepes, do not maintain buffer capacity over multiple uses. These buffers are not permanently immobilized within the polyurethane matrix. The chemical formulas of tris buffer, MES buffer and Hepes buffer are set forth in FIG. 2A. As illustrated in FIG. 2B, the lone amino group of tris buffer reacts with the isocyanate prepolymer and thereby loses its buffer capacity.

Thus, reactive buffers with at least one reactive functional group and one additional buffer group are preferred for co-immobilization in the present invention via covalent bonding. Buffers of this type include, but are not limited to, bis-tris propane, gly-gly, SSC, tricine, or any polypeptide or protein with amine functionality.

Example 2

Physical Properties and Buffer Capacity of Buffer Immobilized Polymers

Although the bis-tris polymer synthesized in Example 1 exhibited reusable buffer capacity, the polymer properties were poor, particularly at higher buffer capacity. Thus, we undertook studies to produce polymers with desirable physical properties such as relatively low density and relatively high porosity. We synthesized an array of polymers prepared using the known one-step syntheses and using a novel two-step synthesis of the present invention. For polymers prepared using the known, one-step method, we used a synthesis method similar to that described in LeJeune et. al. (1997). We found that polymers below 2% bis-tris propane by weight had acceptable physical properties. However, polymers appeared rigid and dense when the amount of bis-tris propane was in the range of 3 to 4 weight percent. Above 4 weight percent bis-tris propane, polymers synthesized in the one-step synthesis gelled into a dense and sticky mass.

For representative immobile buffer polymers prepared using the two-step method of the present invention, we reacted bis-tris propane buffer with isocyanate prepolymer to create a modified prepolymer prior to polymer synthesis. In the first step of one such synthesis, 12 grams of bis-tris propane was added to 40 grams of Hypol 3000 in a plastic reaction vessel. The mixture was stirred for 30 seconds at 2500 rpm and incubated at room temperature for 20 minutes. In the second step, 40 grams of Hypol 3000 and 40 milliliters of 1% PLURONIC® F127 surfactant (nonionic surfactant available from BASF Corp.) solution was added. The mixture was stirred for no longer than 6 seconds at 2500 rpm.

Figure 3:
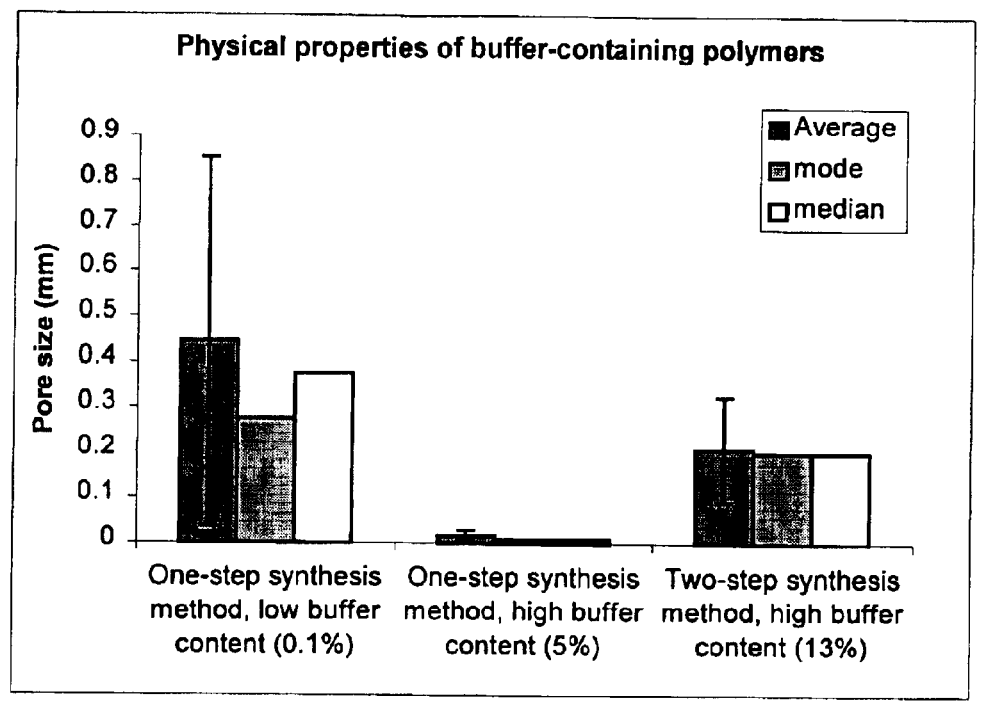
FIG. 3 illustrates that bis-tris propane buffer polymers of the present invention have a desirably high degree of porosity.

FIG. 3 compares the pore size of immobile buffer polymers prepared using one- and two-step synthesis procedures. Immobile buffer (for example, 13% buffer by weight) polymers produced using a two-step reaction scheme have low density and are highly porous. In contrast, polymers containing 4 weight percent or higher bis-tris propane prepared using a one-step synthesis technique have poor physical properties.

Figure 4:
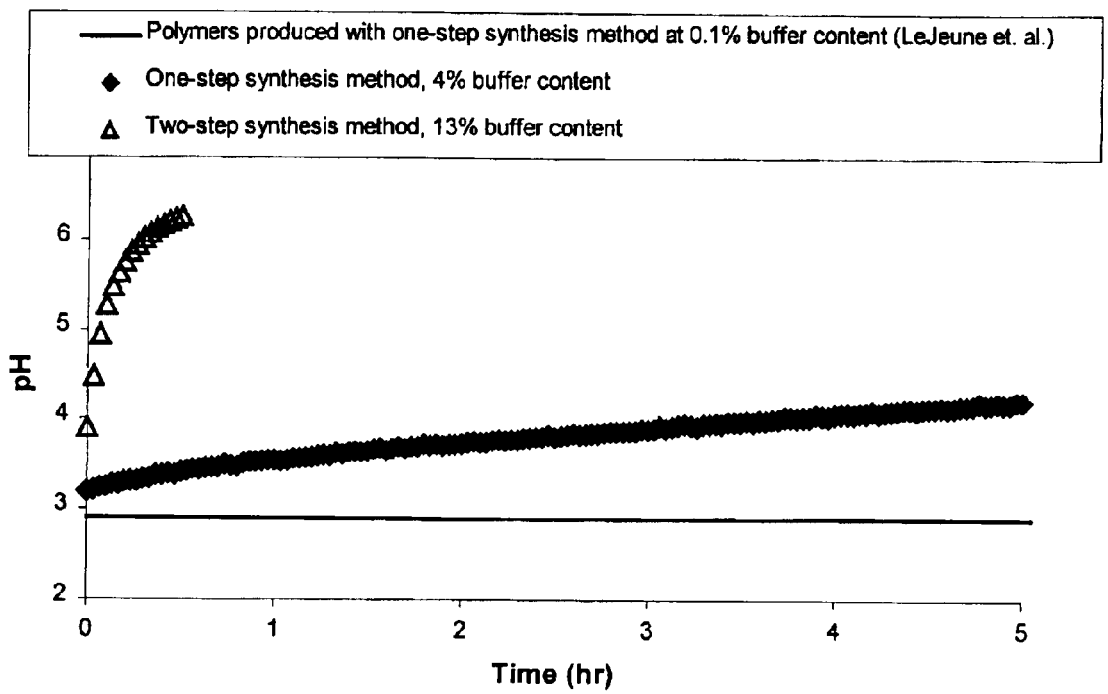
FIG. 4 illustrates that a buffer immobile polymer of the present invention quickly raises pH, while a polymer prepared using a current or prior synthetic method takes hours to raise pH.

We also studied the rate at which the buffer polymers buffer 2 mM acid. In several studies, we placed 200 milligrams of a polymer prepared using a two-step synthesis procedure and having 13% by weight buffer content in 100 ml of 2 mM hydrochloric acid. We also placed 200 milligrams of a polymers synthesized using a one-step synthesis procedure and having 4% or 0.1% by weight bis-tris propane buffer in 100 ml of 2 mM hydrochloric acid. FIG. 4 and Table 4 show that "two-step polymers" of the present invention quickly neutralize acid solution, raising the pH to around 6.5 within minutes. FIG. 4 and Table 4 also show that two-step buffer-containing polymers neutralize pH 3 to pH 4 in seconds. The pH of a solution containing a "one-step polymer" at 4% buffer content rises to 3.5 after thirty minutes and to 4 after several hours. The pH of a solution containing a "one-step polymer" at 0.1% buffer content does not increase.

TABLE 4

Buffer-containing polymers prepared using a two-step synthesizing method neutralize pH 3 to pH 4 in seconds.
Time required to neutralize pH 3 to pH 4 with buffer-containing polymers.

| 0.1% buffer prepared using a one-step synthesizing method | 4% buffer prepared using a one-step synthesizing method | 13% buffer prepared using a two-step synthesizing method |
|---|---|---|
| DOES NOT NEUTRALIZE ACID | 4 hours | 10 seconds |

Figure 5:
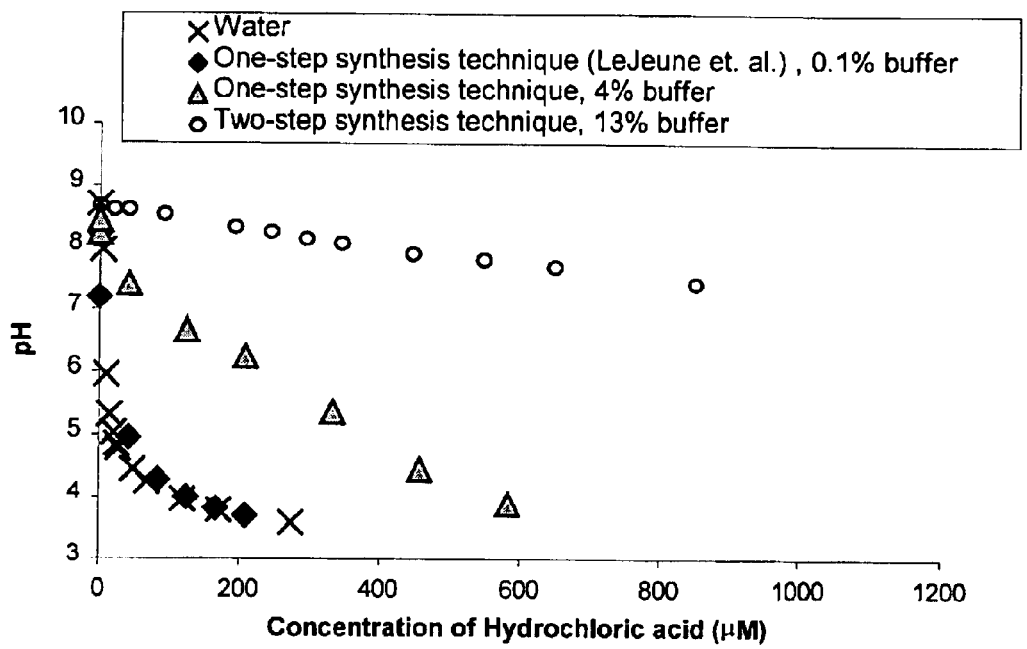
FIG. 5 illustrates that bis-tris propane buffer containing polymers provide a high buffer capacity, as indicated by titration with 3.8% hydrochloric acid.

We also determined the buffer capacity of buffer polymers produced using a two-step synthesis procedure as compared to polymers prepared using a one-step procedure. In several studies, we added similar amounts (approximately 400 mg) of each type of polymer to 100 milliliters tap water. We subsequently added small aliquots of hydrochloric acid (3.8%) and monitored the pH. As illustrated in FIG. 5, the "two-step polymers" of the present invention maintained a high pH even after the addition of 800 $\mu M$ acid. On the other hand, the pH of "one-step polymers" quickly drops to around 3.7.

Table 5 summarizes a comparison of physical properties, buffer capacity, and reusability for polymers produced using the current one-step synthesis method and the two-step synthesis method of the present invention. The synthetic method of the present invention yields buffer polymers capable of neutralizing large amounts of acid or base. Moreover, buffer polymers synthesized using the two-step synthesis method of the present invention have good physical properties and can be reused repeatedly without losing buffer capacity.

TABLE 5

Properties of various polyurethane foam polymers.

| Buffer polymer synthesis | Physical properties | Buffer capacity | Reusability |
|---|---|---|---|
| One-step synthesis Reactive or unreactive buffer Containing 0 to 4% wt. buffer | Porous polymer $Pore_{AVG} = 0.2–0.6$ mm $\rho_{polymer} = 0.10$ g/cm$^3$ | LOW pH of 3.1 in 1 mM HCl pH of 2.9 in 2 mM HCl | Yes |
| One-step synthesis Unreactive buffer Containing greater than 5% wt. buffer | Porous polymer $Pore_{AVG} = 0.2–0.6$ mm $\rho_{polymer} = 0.10$ g/cm$^3$ | Free buffer only; Polymer loses buffer capacity after one use | No |
| One-step synthesis Reactive buffer Containing greater than 5% wt. buffer | Nonuniform mixture $Pore_{AVG} = 0.01$ mm $\rho_{mixture} = 0.83$ g/cm$^3$ | N/A Dense polymer, not a foam | N/A |
| Two-step synthesis (with a buffer treatment step) Reactive buffer Containing up to 15% wt. buffer | Porous polymer $Pore_{AVG} = 0.2–0.3$ mm $\rho_{polymer} = 0.18$ g/cm$^3$ | HIGH pH of 7 in 1 mM HCl pH of 7 in 2 mM HCl | Yes |

Figure 6:
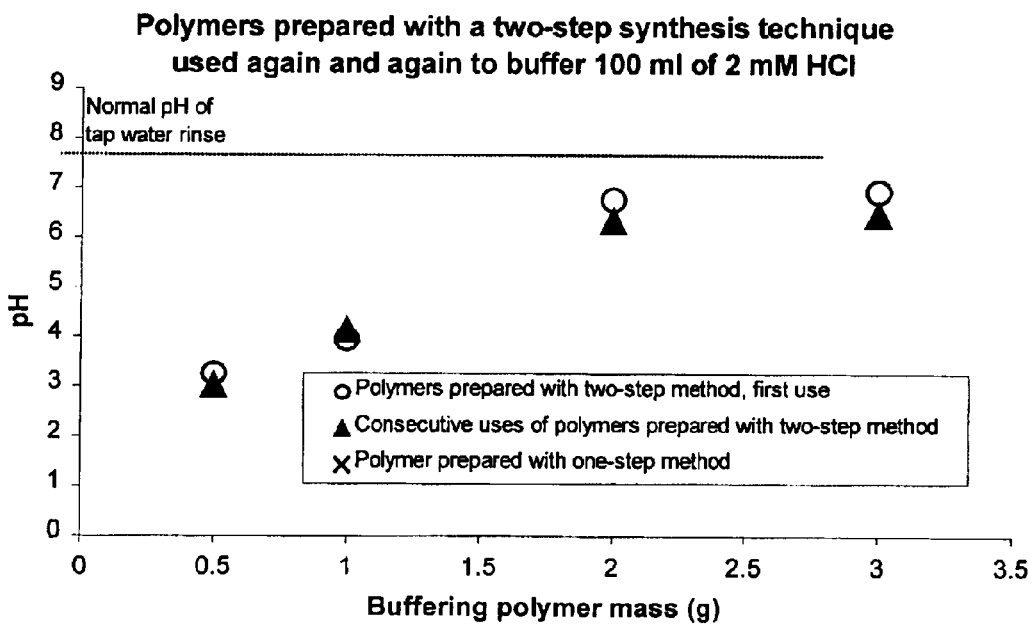
FIG. 6 illustrates the reusable buffer capacity of buffer-containing polymers of the present invention.

We studied the degree of reusable buffer capacity contained within immobile buffer polymers. In such studies, we inserted various amounts of bis-tris buffer polymer described above in 100 milliliters of 2 mM hydrochloric acid and followed the pH until it reached equilibrium. We found that around 2 grams of polymer in 100 ml solution (20 milligrams polymer per milliliter solution) is required to maintain a pH above 6. We then removed the polymer, placed it in a dishwasher with water at 55° C., and allowed the polymer to dry. We repeated the experiment, placing the washed polymer into 100 ml of 2 mM acid as before. This process was repeated three times. The results (illustrated in FIG. 6) demonstrated that buffer polymers prepared using the two-step synthesis method of the present invention are completely reusable.

Example 3

Synthesis of Enzyme Containing Buffering Polymers

We synthesized polymers incorporating buffer and enzyme using a one-step synthesis technique similar to that described in LeJeune et. al (1997). In one such synthesis, the enzyme solution contained 10 mM buffer (pH 8.0), 1% PLURONIC F68 surfactant (available from BASF), and up to several percent by weight enzyme. In general, any nonionic surfactant is suitable for use in the present invention. Equal parts Hypol 3000 prepolymer and enzyme-buffer aqueous solution were stirred with mixer head for 20 seconds at 2500 rpm. Although the polymers synthesized in such a one-step synthesis contain immobilized buffer and enzyme, we do not generally refer to those polymers as co-immobile buffer and enzyme polymers because their buffer capacity is very low.

In several studies of the two-step, co-immobile buffer and enzyme synthesis methods of the present invention, we used a three phase reaction mixture of Hypol 3000 prepolymer (1 part), aqueous enzyme solution containing 1% PLURONIC F127 surfactant (1 part) (available from BASF), and pretreated buffer mixture (1.3 parts) As with two-step buffer polymers described in Example 1, synthesis of two-step co-immobile buffer and enzyme polymers utilize a two-step reaction synthesis method in which buffer was reacted with prepolymer prior to polymer synthesis. In synthesis of co-immobile buffer and enzyme polymers of the present invention, however, enzyme is added to aqueous solution in the second step. The co-immobile buffer and enzyme polymers of the present invention had similar physical properties to the "two-step" buffer polymers described in Example 1.

Example 4

Increased Enzyme Activity and Stability in Extreme pH

Figure 7:
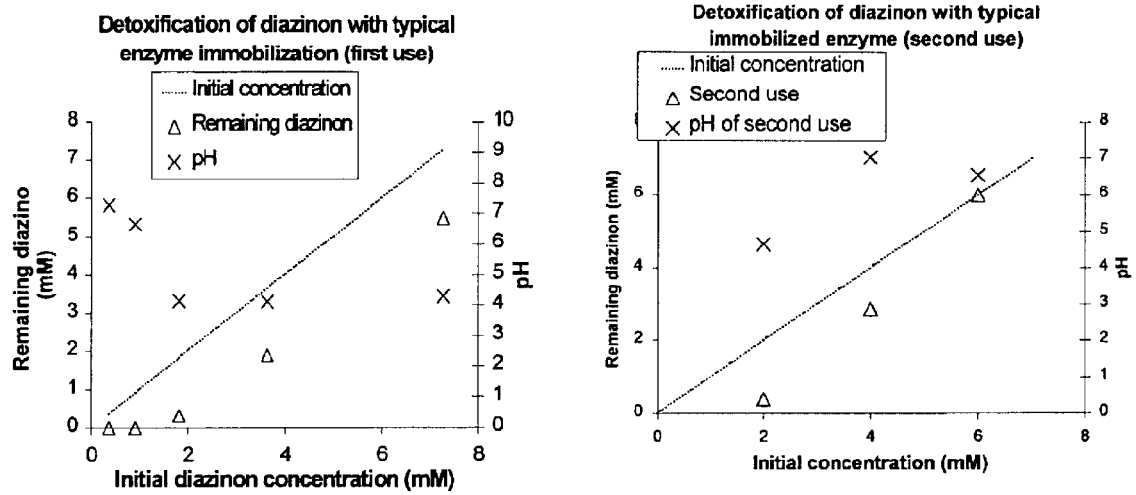
FIG. 7 illustrates that a co-immobile buffer and OPH enzyme polymers (BEP) of the present invention protects against acid attack, and that the co-immobilized buffer and enzyme polymers are reusable.

Immobilized OPH enzyme prepared using typical or current one-step synthesis methods denature quickly as the pH is lowered. Moreover, activity cannot be regenerated if the pH of the environment is sufficiently low. As illustrated in FIG. 7, OPH enzyme polymers prepared with a current synthesis method as described above do not detoxify a significant amount of diazinon. Additionally, acid produced during hydrolysis denatures the enzyme such that it has no activity when used again. Above 4 mM diazinon, such enzyme polymers have little activity after one use.

Figure 8:
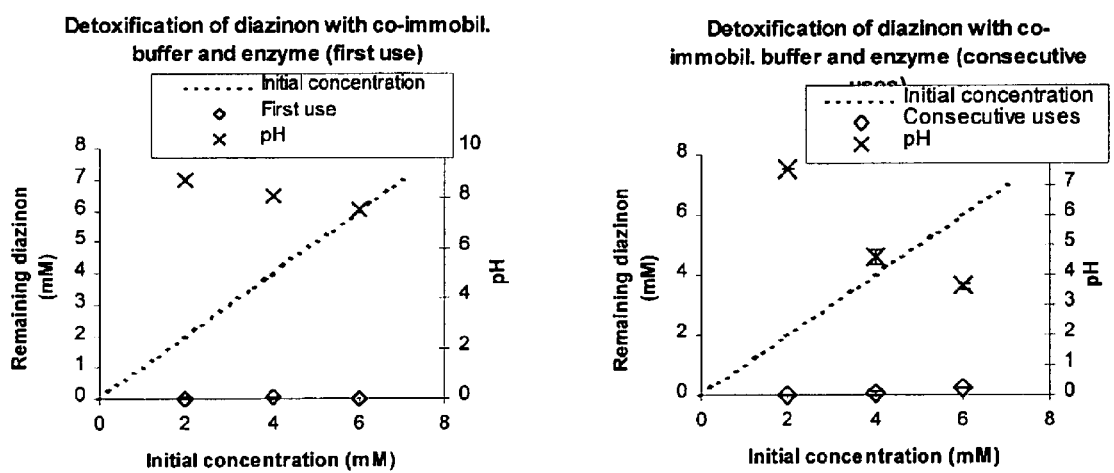
FIG. 8 illustrates that OPH enzyme polymers (without buffer) cannot be reused.

As illustrated in FIG. 8, when a similar experiment is performed using the co-immobile buffer and enzyme polymers of the present invention, there is no loss in overall activity. In general, the co-immobilized buffer prevent the immobilized enzyme from denaturing by maintaining a relatively high pH.

Example 5

Increased hydrolase Enzyme Performance

Comparing co-immobilized buffer and hydrolase enzyme polymer (synthesized as a fabric) to polymer synthesized under current methods demonstrated that activity levels are significantly increased in unbuffered solutions for the co-immobilized buffer and hydrolase enzyme polymers of the present invention. Unlike native enzymes and enzymatic polymers synthesized using current methods, suitable pH for high enzymatic catalytic rates is maintained throughout the course of reaction with the co-immobilized buffer and hydrolase enzyme polymer of the present invention.

Figure 9A:
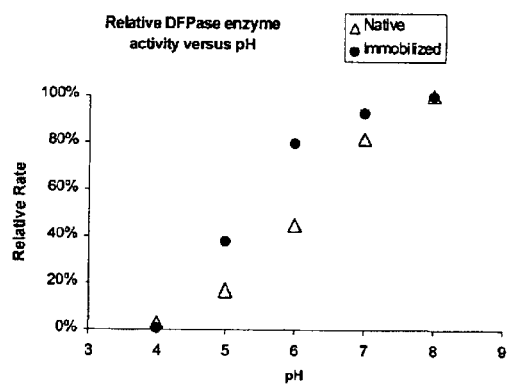
FIGS. 9A and 9B, respectively, illustrate the pH-dependence of native DFPase and organophosphorous hydrolase (OPH) enzymes in solution.
Figure 9B:
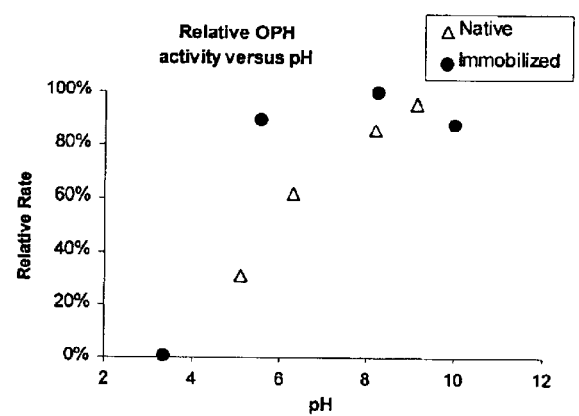
Figure 10B:
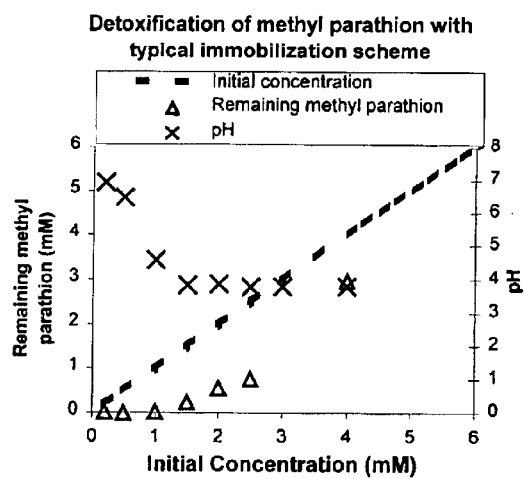
FIG. 10B illustrates that immobilized enzyme (OPH) (without immobilized buffer) can hydrolyze only low concentrations of substrate as a result of production of excess acidic byproduct.
Figure 10A:
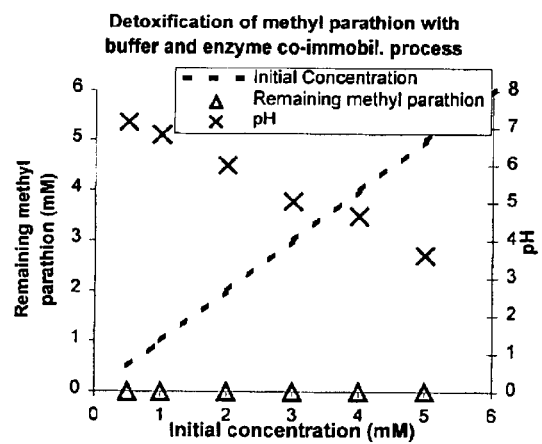
FIG. 10A illustrates that co-immobile buffer and enzyme (OPH) polymers of the present invention provide sufficient buffer capacity to maintain neutral pH's in solutions with high substrate concentrations.

As illustrated in FIGS. 9A and 9B respectively, catalytic activity peaks at approximately pH 8, and activity ceases at approximately pH 4 with DFPase and organophosphorous hydrolase enzymes. As illustrated in FIG. 10A, however, the co-immobile buffer and OPH enzyme polymers of the present invention maintain a more neutral pH while hydrolyzing 5 mM methyl parathion. As illustrated in FIG. 10B, OPH enzyme polymers prepared using a current, one-step synthesis method hydrolyze only about 1 mM methyl parathion because of a low pH environment.

Example 6

Utility as a Substrate Removal and Detoxifying Pad

Figure 11A:
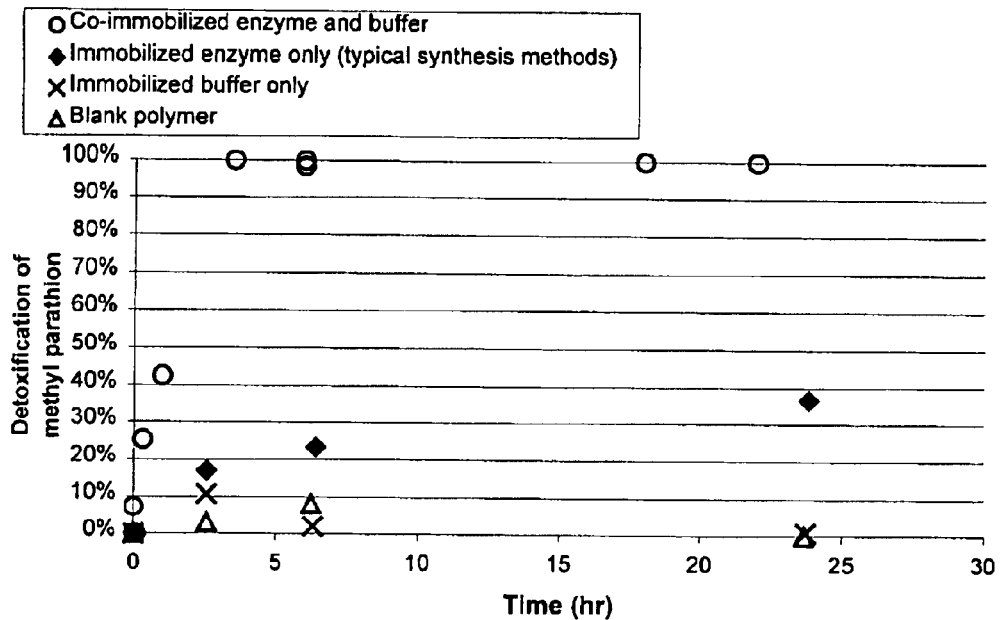
FIG. 11A illustrates that a co-immobile OPH enzyme and buffer pad of the present invention quickly detoxifies removed parathion, while immobile OPH enzyme (without immobilized buffer) does not.
Figure 11B:
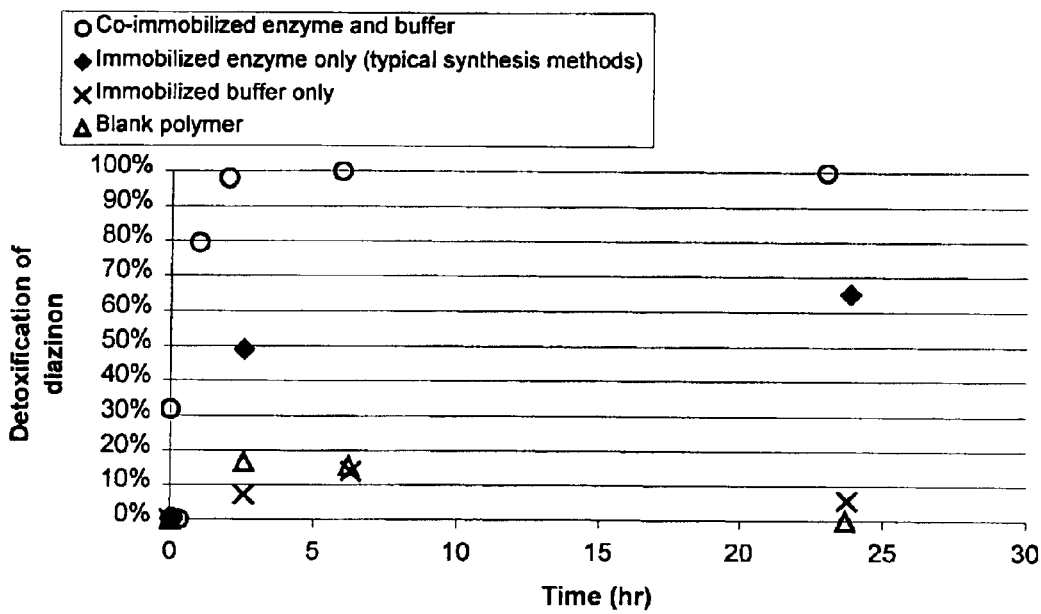
FIG. 11B illustrates that a co-immobile OPH enzyme and buffer pad of the present invention quickly detoxifies removed diazinon, while immobile OPH enzyme (without immobilized buffer) does not.
Figure 11C:
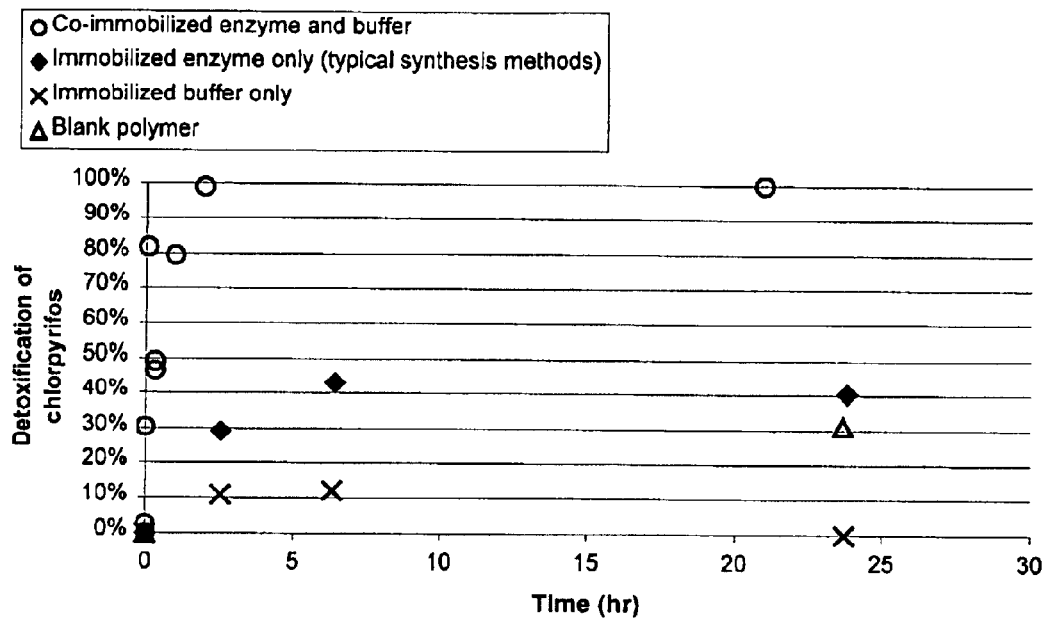
FIG. 11C illustrates that a co-immobile OPH enzyme and buffer pad of the present invention quickly detoxifies removed chlorpyrifos, while immobile OPH enzyme (without immobilized buffer) does not.

When used as decontaminating and detoxifying surface wipes against organophosphorous pesticide contamination, co-immobilized buffer and OPH enzyme polymers of the present invention are once again effective at maintaining both high activity and neutral pH. In several studies, glass surfaces were contaminated with 10 mg methyl parathion. We activated both co-immobile buffer and enzyme polymer pads of the present invention as well as immobile enzyme (without buffer) pads by moistening with tap water. The moist polymers were used to wipe contaminated surfaces and set aside for various periods of time. Samples were extracted with solvent and analyzed with chromatography. Both co-immobile buffer/enzyme pads and immobile enzyme (without buffer) pads completely cleaned the surfaces. However, only the co-immobile buffer and enzyme pads of the present invention completely detoxified the removed pesticide. FIGS. 11A through 11C show that 90% detoxification occurs in less than 1 hour and 100% detoxification occurs in less than 2 hours with co-immobile buffer and enzyme polymers. As illustrated in FIG. 11A, a co-immobilized enzyme and buffer containing polymer pad (2 g) detoxified 100% of methyl parathion (10 mg active ingredient) in 3 hours, while polymers prepared by typical or current synthesis achieve only 40% in 24 hours. As illustrated in FIG. 11B, a co-immobilized enzyme and buffer containing polymer pad (2 g) detoxified 100% of diazinon (10 mg active ingredient) in 2 hours. As illustrated in FIG. 11C, a co-immobilized enzyme and buffer containing polymer pad (2 g) detoxified 100% of chlorpyrifos (100 mg active ingredient) in 2 hours. Other polymers were unable to achieve these high levels of detoxification. Once again, the co-immobile buffer and enzyme polymer pads of the present invention neutralize byproduct acid produced during the reaction.

The co-immobile buffer and enzyme polymers of the present invention are also useful as detoxifying surface wipes against simulated pesticide spills and equipment contamination. In that regard, we simulated pesticide spills by pouring diluted and concentrated pesticide formulations onto surfaces and using the co-immobile enzyme and buffer containing polymer pads as absorbents. We simulated equipment cleanup by first contaminating smooth metal surfaces with a light spray of either dilute or concentrated pesticide formulation. After treatment with the pads, we quantified residual pesticide after 6 hours. As set forth in Tables 6 and 7, the surfaces were effectively cleaned and approximately 100% (+/−3% for methyl parathion, +/−0.1% for diazinon) of removed contamination was detoxified. Once again, neutral pH was maintained throughout the reaction with the co-immobile buffer and enzyme polymers of the present invention.

TABLE 6

Methyl parathion contaminated surfaces are cleaned, and removed pesticide is detoxified within hours.

| Methyl parathion | Equipment cleanup, dilute | Spill, dilute | Equipment cleanup, concentrate | Spill, concentrate |
|---|---|---|---|---|
| Conc. of simulant ($\mu$M) | 83 | 359 | 3680 | 4770 |
| Amt. of simulant added (ml) | 1 | 1 | 1 | 10 |
| Methyl parathion added ($\mu$g) | 21.8 | 94.4 | 967.8 | 12,545 |
| Cleaning efficiency (%) | 100% | >99% | 100% | 100% |
| Detoxification level (%) | 100% | 100% | 100% | 100% |

TABLE 7

Diazinon contaminated surfaces are cleaned, and removed pesticide is detoxified within hours.

| Diazinon | Equipment cleanup, dilute | Spill, dilute | Equipment cleanup, concentrate | Spill, concentrate |
|---|---|---|---|---|
| Conc. of loading solution ($\mu$M) | 90 | 237 | 2080 | 4830 |
| Amt. of simulant added (ml) | 1 | 1 | 1 | 10 |
| Methyl parathion added ($\mu$g) | 27.4 | 72.0 | 632.3 | 14,683 |
| Cleaning efficiency (%) | 100% | 100% | 100% | 100% |
| Detoxification level (%) | 100% | 100% | 100% | 100% |

Figure 12A:
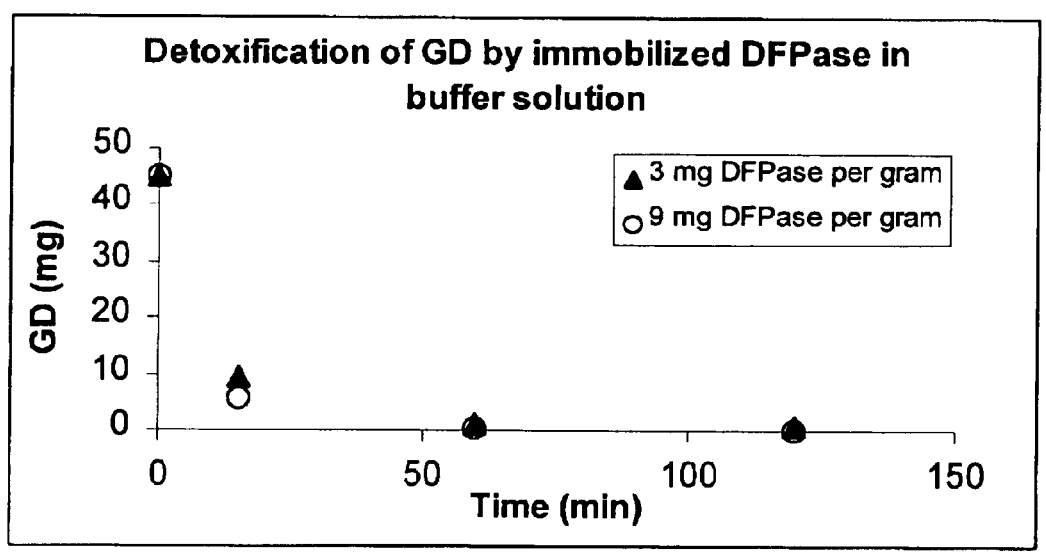
FIG. 12A illustrates that immobilized DFPase enzyme quickly hydrolyzes soman (GD) in 50 mM tris buffer.
Figure 12B:
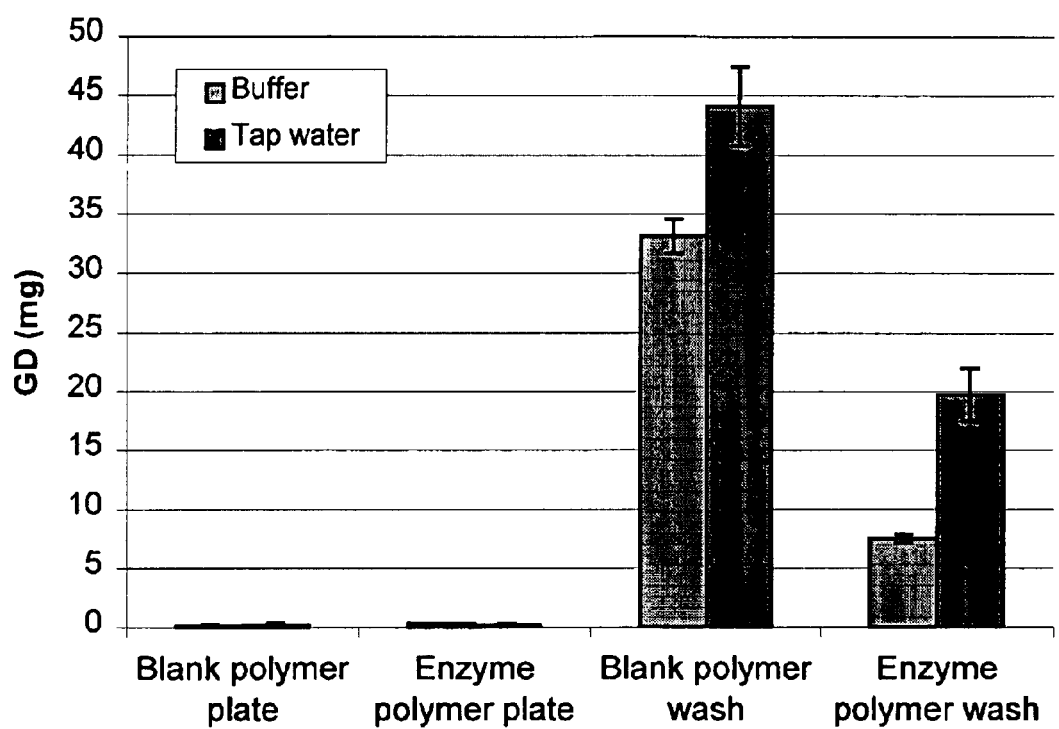
FIG. 12B illustrates that immobilized DFPase enzyme has little or no activity on soman (GD) in unbuffered solution (tap water).
Figure 12C:
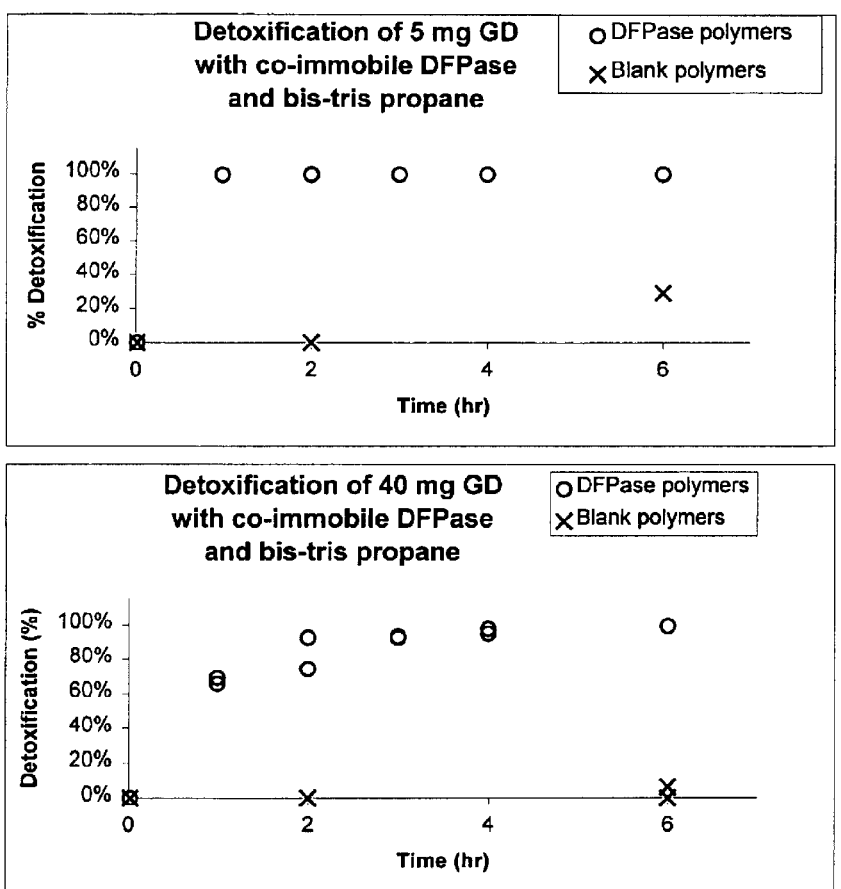
FIG. 12C illustrates that co-immobile bis-tris propane and DFPase enzyme polymer of the present invention quickly hydrolyzes soman (GD) in unbuffered solution (tap water).

In addition to applications involving pesticides, we have demonstrated that the co-immobile buffer and enzyme polymers of the present invention have utility against chemical nerve agents. We tested the co-immobile buffer and enzyme polymers against soman (GD) in an unbuffered environment. Approximately 1 gram of co-immobile bis-tris propane buffer and DFPase (4.3 mg enzyme per gram polymer) were moistened with tap water and used to clean and detoxify soman. We also tested two control reactions. We tested approximately 1 gram of immobilized DFPase in buffer (3 and 9 mg enzyme per gram polymer) as well as immobilized DFPase in tap water (3 mg enzyme per gram polymer) against soman. Comparing results from control reaction (FIGS. 12A and 12B) to results with co-immobile buffer and enzyme polymers (FIG. 12C), we found that only the co-immobile buffer and enzyme polymers of the present invention are effective in an unbuffered environment. Immobile DFPase (without buffer) in tap water has little or no activity on soman. FIG. 12C also shows that the co-immobile buffer and enzyme polymers of the present invention effectively clean contamination off of surfaces.

Example 7

Utility as Catalytic Filter

Figure 13A:
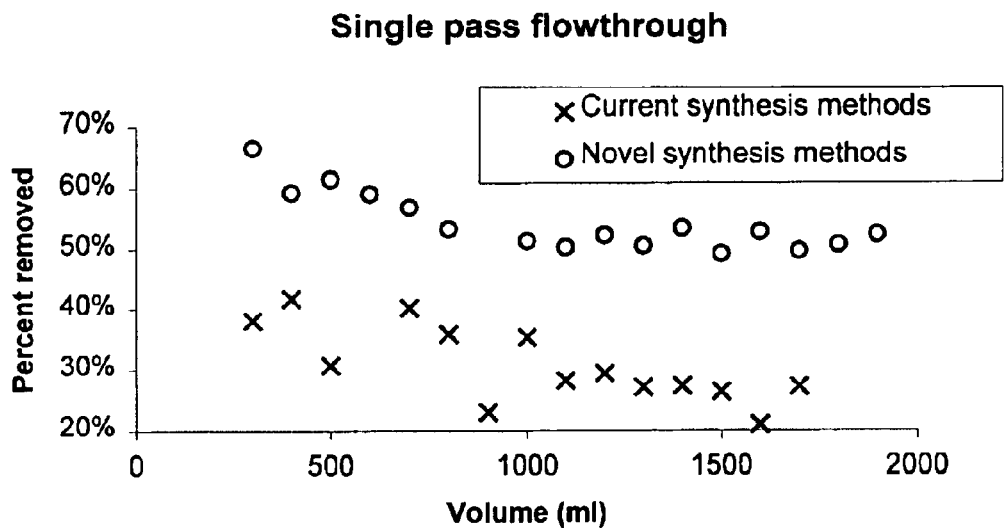
FIG. 13A illustrates that polyurethane polymers, including polymers with immobilized buffer, can be used as filters.
Figure 13B:
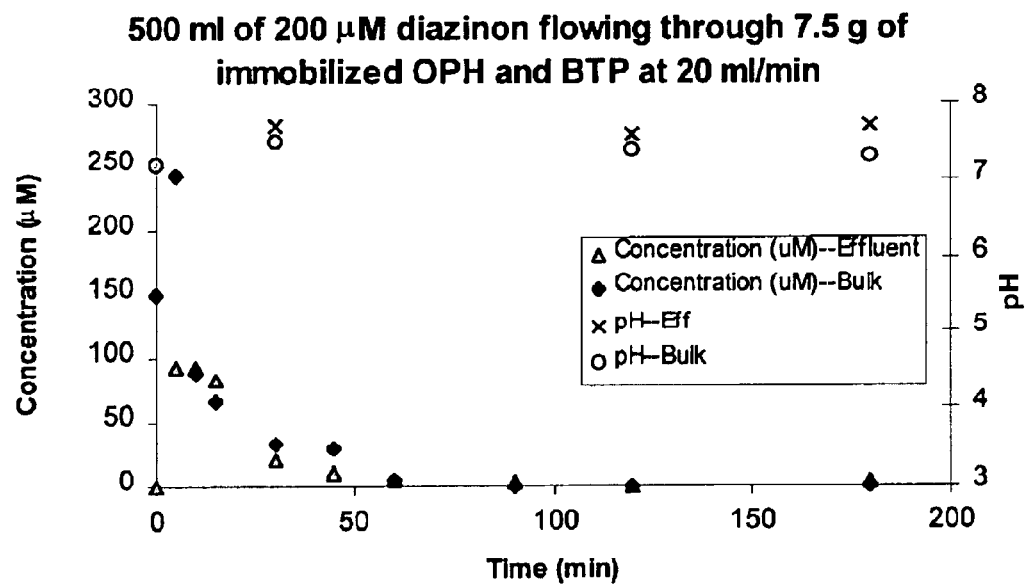
FIG. 13B illustrates that co-immobile buffer and OPH enzyme polymers of the present invention are effective for use as a catalytic filter against diazinon.
Figure 13C:
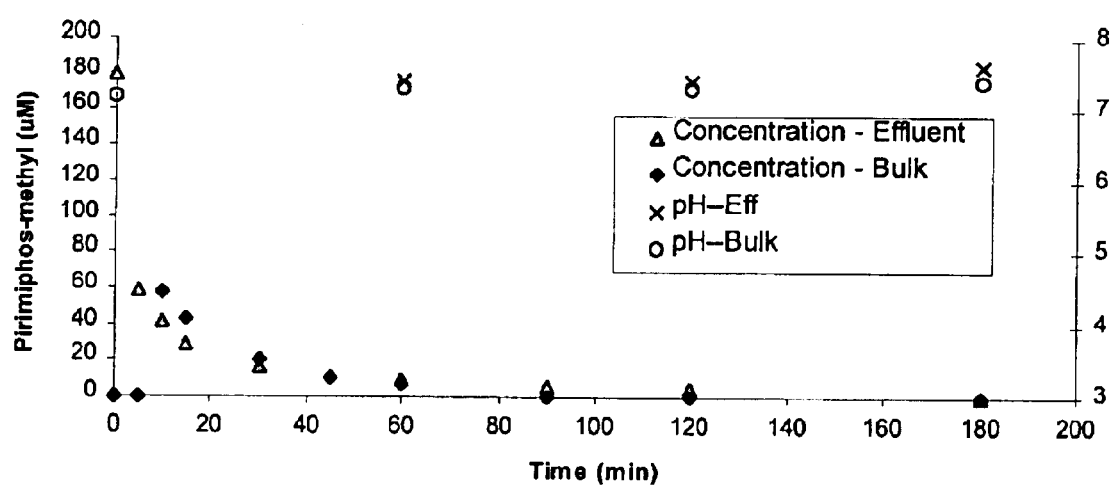
FIG. 13C illustrates that co-immobile buffer and OPH enzyme polymer s of the present invention are effective for use as a catalytic filter against pirimiphos-methyl.

When used as a filter in single pass and looped flowthroughs, hydrolase enzyme co-immobilized with buffer quickly degraded removed substrate into byproduct. The co-immobile buffer and enzyme polymer fabrics of the present invention effectively captured insoluble particulates (see FIG. 13A). Immobilized enzyme(s) within the polymer detoxified soluble substrate while immobilized buffer neutralized byproduct acid or base, maintaining a suitable pH for catalytic activity. Following degradation by immobile enzyme and pH neutralization by immobile buffer, captured insoluble substrate solubilized by means of a concentration gradient. The process was repeated until all captured substrate was detoxified by enzyme. FIG. 13B shows that a co-immobile buffer and OPH polymer of the present invention filtered and detoxified diazinon while maintaining neutral pH. FIG. 13C shows that co-immobile buffer and OPH polymer of the present invention filtered and detoxified pirimiphos-methyl while maintaining neutral pH.

The foregoing description and accompanying drawings set forth the preferred embodiments of the invention at the present time. Various modifications, additions and alternative designs will, of course, become apparent to those skilled in the art in light of the foregoing teachings without departing from the scope of the disclosed invention. The scope of the invention is indicated by the following claims rather than by the foregoing description. All changes and variations that come within the meaning and range of equivalency of the claims are to be embraced within their scope.

What is claimed is:

1. A polyurethane polymer comprising: at least one buffer selected to adjust pH to a pH within a desired range, the buffer compound being immobilized within the polymer; the polymer having a buffer capacity in excess of 3 micromoles of acid or base per gram polymer.

2. The polyurethane polymer of claim 1 wherein the polymer has a buffer capacity in excess of 60 micromoles acid or base per gram polymer.

3. The polyurethane polymer of claim 2 wherein the polymer has a buffer capacity in excess of 200 micromoles acid or base per gram polymer.

4. A method for preparing a polyurethane polymer immobilizing at least one buffer comprising the steps:

reacting a buffer compound with a multifunctional precursor for the polyurethane polymer to produce a modified precursor, the buffer compound having at least one functional group for reacting with the precursor and at least one buffering group that remains functional as a buffer after the buffer compound is reacted with the precursor; and subsequent to reacting the buffer compound with the precursor, polymerizing the modified precursor to form the polyurethane polymer.

5. The method of claim 4 wherein the polymer is formed by first reacting the buffer compound with an isocyanate functionalized polyurethane precursor to produce a modified polyurethane precursor.

6. The method of claim 5 wherein water and the modified polyurethane precursor are mixed to form the polymer.

7. A polymer comprising:

at least one enzyme that is selected to catalyze a reaction of a substance, the enzyme being immobilized within the polymer; and at least one buffer selected to adjust the pH in the vicinity of the enzyme to a pH within a desired range, the buffer compound being immobilized within the polymer;

the polymer having enzyme activity, and a buffer capacity in excess of 3 micromoles acid or base per gram polymer.

8. A polymer comprising:

at least one enzyme that is selected to catalyze a reaction of a substance, the enzyme being covalently bonded to the polymer; and at least one buffer selected to adjust the pH in the vicinity of the enzyme to a pH within a desired range, the buffer being covalently bonded to the polymer;

the polymer having enzyme activity, and a buffer capacity in excess of 3 micromoles acid or base per gram polymer.

9. The polymer of claim 8 wherein the polymer has enzyme activity, and a buffer capacity in excess of 60 micromoles acid or base per gram polymer.

10. The polymer of claim 8 wherein the polymer has enzyme activity, and a buffer capacity in excess of 100 micromoles acid or base per gram polymer.

11. The polymer of claim 8 wherein the polymer has enzyme activity, and a buffer capacity in excess of 200 micromoles acid or base per gram polymer.

12. The polymer of claim 8 wherein the polymer is a polyurethane.

13. The polymer of claim 12 wherein the polyurethane is a foam having an average pore size of at least approximately 0.1 mm.

14. The polymer of claim 12 wherein the polyurethane is a foam having an average pore size of at least approximately 0.2 mm.

15. The polymer of claim 12 wherein the polyurethane is a foam having a density no greater than approximately 0.4 g/cm³.

16. The polymer of claim 12 wherein the polyurethane is a foam having a density no greater than approximately 0.2 g/cm³.

17. The method of claim 8 wherein the enzyme is a hydrolase enzyme.

18. A system for catalyzing a reaction of at least one substance in an environment, the system comprising:
    at least one enzyme that is selected to catalyze a reaction of the substance; and
    at least one buffer compound selected to adjust the pH in the vicinity of the enzyme to a pH within a desired range;
each of the enzyme and the buffer compound being covalently bonded within a single polymer, the polymer having enzyme activity, and a buffer capacity in excess of 3 micromoles acid or base per gram polymer.

19. The system of claim 18 wherein the single polymer is a polyurethane.

20. The system of claim 19 wherein the polyurethane is a foam having an average pore size of at least approximately 0.1 mm.

21. The system of claim 19 wherein the polyurethane is a foam having an average pore size of at least approximately 0.2 mm.

22. The system of claim 19 wherein the polyurethane is a foam having a density no greater than approximately 0.4 g/cm³.

23. The system of claim 19 wherein the polyurethane is a foam having a density no greater than approximately 0.2 g/cm³.

24. The system of claim 18 wherein the enzyme is a hydrolase enzyme.

25. A method for preparing a polymer immobilizing at least one enzyme and at least one buffer comprising the steps:
    reacting a buffer compound with a multifunctional precursor for the polymer to produce a modified precursor, the buffer compound having at least one functional group for reacting with the precursor and at least one buffering group that remains functional as a buffer after the buffer compound is reacted with the precursor; and
    subsequent to reacting the buffer compound with the precursor, polymerizing the modified precursor in the presence of the enzyme to bond the enzyme to the polymer.

26. The method of claim 25 wherein the polymer is a polyurethane.

27. The method of claim 26 wherein the polymer is formed by first reacting the buffer compound with an isocyanate functionalized polyurethane precursor to produce a modified polyurethane precursor.

28. The method of claim 27 wherein the enzyme, water and the modified polyurethane precursor are mixed to form the polymer.

29. The method of claim 25 wherein the enzyme is a hydrolase enzyme.

30. The method of claim 28 wherein the enzyme is a hydrolase enzyme.

31. A method for preparing a modified polymer precursor for synthesis of a buffer immobilizing polymer comprising the step:
    reacting a multifunctional buffer compound with a multifunctional precursor for the polymer to covalently bond the buffer compound to the precursor compound via reaction of one of the functional groups of the buffer compound with one of the function groups of the polymer precursor, thereby producing the modified polymer precursor, the attached buffer compound having at least one functional group remaining after attachment that retains buffer capacity, the modified polymer precursor retaining at least one functional group thereon suitable to react in a subsequent polymerization to synthesize the buffer immobilizing polymer.

32. The method of claim 31 wherein the multifunctional polymer precursor includes at least one isocyanate group.

* * * * *